United States Patent
Chou et al.

(10) Patent No.: US 7,705,978 B2
(45) Date of Patent: Apr. 27, 2010

(54) METHOD AND APPARATUS FOR INSPECTION OF MULTI-JUNCTION SOLAR CELLS

(75) Inventors: Mau-Song Chou, Rancho Palos Verdes, CA (US); Jonathan W. Arenberg, Santa Monica, CA (US); Mark A. Menard, Chino Hills, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 1117 days.

(21) Appl. No.: 11/348,019

(22) Filed: Feb. 6, 2006

(65) Prior Publication Data

US 2007/0181180 A1  Aug. 9, 2007

(51) Int. Cl.
  *G01N 21/88* (2006.01)
  *G02F 1/01* (2006.01)
(52) U.S. Cl. ............... 356/237.3; 356/237.2; 250/330; 250/331
(58) Field of Classification Search ... 356/237.1–237.3, 356/4.07; 250/341.1, 330, 223 B, 559.45
See application file for complete search history.

(56) References Cited

U.S. PATENT DOCUMENTS

| | | | |
|---|---|---|---|
| 4,547,073 A | 10/1985 | Kugimiya | |
| 4,794,264 A | 12/1988 | Quackenbos et al. | |
| 4,794,265 A | 12/1988 | Quackenbos et al. | |
| 4,975,568 A * | 12/1990 | Taniguchi et al. | 250/223 B |
| 5,018,867 A | 5/1991 | Piironen | |
| 5,028,129 A * | 7/1991 | Smith | 356/4.07 |
| 5,334,844 A | 8/1994 | Pollard et al. | |
| 5,367,174 A * | 11/1994 | Bazile et al. | 250/559.45 |
| 5,640,237 A | 6/1997 | Esrig et al. | |
| 5,822,054 A | 10/1998 | Coulthard | |
| 6,111,638 A | 8/2000 | Chou et al. | |
| 6,236,044 B1 | 5/2001 | Chou et al. | |
| 6,420,705 B2 | 7/2002 | Chou et al. | |
| 6,433,867 B1 | 8/2002 | Esquivel | |
| 6,614,519 B1 | 9/2003 | Latta et al. | |

(Continued)

FOREIGN PATENT DOCUMENTS

EP   1 416 288 A1   5/2004

(Continued)

OTHER PUBLICATIONS

J.R. Hodor et al., "Optical sensor designs for the detection of cracks in optical materials," SPIE Vo. 1168 Current Devopments in Optical Eng. & Comm. Optics, 138-146 (1989).

(Continued)

*Primary Examiner*—Sang Nguyen
(74) *Attorney, Agent, or Firm*—Carmen Patti Law Group, LLC

(57) ABSTRACT

A technique for providing high-contrast images of defects in solar cells and solar panels, by illuminating each cell under inspection with broadband infrared radiation, and then forming an image of radiation that is secularly reflected from the cell. Multi-junction solar cells have a metal backing layer that secularly reflects the illumination back into an appropriately positioned and aligned camera, selected to be sensitive to infrared wavelengths at which the solar cell materials are relatively transparent.

18 Claims, 2 Drawing Sheets

U.S. PATENT DOCUMENTS 6,816,249 B2 11/2004 Fairley et al.
7,326,929 B2 * 2/2008 Chou et al. ................. 250/330
2006/0278831 A1 * 12/2006 Matsumoto et al. ...... 250/341.1

FOREIGN PATENT DOCUMENTS

JP 2007 078404 3/2007

OTHER PUBLICATIONS

J.R. Hodor et al., "Infrared techniques applied to large solar arrays," SPIE vol. 1540 Infrared Technology XVII 331-337 (1991).

A. Scott, "Instrument for the measurement of specular reflectivity of bright metal surfaces," J. Scientific Instruments 37, 435-438 (1960).

Jennings C M et al; Portable Infrared Optical Inspection Station for Solar Array Panels; SOL ENG; Solar Engineering 1993; pp. 245-250; ASME; New York, NY; USA.

Paulson R et al; Infrared Techniques Applied to Large Solar Arrays; Proceedings of the SPIE—The International Society for Optical Engineering USA; 1981; pp. 176-186; vol. 304; XP009087290 ISSN: 0277-786X.

Hodor J R et al; Infrared Technology Comes to State-of-the-Art Solar Array Production; Proceedings of the SPIE—The International Society for Optical Engineering USA; 1987; pp. 22-29; vol. 819; XP009087292 ISSN: 0277-786X.

* cited by examiner

US 7,705,978 B2

METHOD AND APPARATUS FOR INSPECTION OF MULTI-JUNCTION SOLAR CELLS

BACKGROUND OF THE INVENTION

This invention relates generally to optical imaging techniques and, more particularly, to techniques for detecting defects in solar cells. Solar cells are widely used on spacecraft and in terrestrial applications for the conversion of energy in the form of sunlight to useful electrical energy. Individual solar cells are typically arrayed in large flat or curved panels to provide power output at more useful levels. Cracks in a solar cell, caused by defective materials or arising during fabrication, have the potential to severely limit the power output of the solar panel that contains such a defective cell. Once a crack has begun, it is highly probable that it will propagate over time to develop into a more significant crack, because solar panels are typically subject to cyclic extremes of temperature. Therefore, it is important to detect not only large cracks and defects but also small ones.

Recently, some advanced multi-junction solar cells, including double- and triple-junction cells, have achieved substantially higher efficiencies than conventional high-efficiency silicon cells. These multi-junction cells utilize several layers of junctions to provide a better match to the solar spectrum. Prior to the present invention, no inspection method could be used for locating defects in multi-junction cells. For example, a method based on the use of a ring illuminator to inspect high efficiency silicon cells, as described in U.S. Pat. Nos. 6,236,044 B1 and 6,420,705 B2, is unable to inspect the multi-junction cells.

There is a related need in the art of making solar panels, to detect micro-cracks that sometimes result from spot-welding of interconnects to solar cells. Spot welding can reduce contamination that might be generated by soldering. Unfortunately, however, spot welding can cause micro-cracks if an electrode exerts too high pressure on the cell. Such micro-cracks are very difficult to detect because they are very small, sometimes less than 1 mm in length. A photo-acoustic method can be used but it is slow and requires water to be sprayed on each cell under inspection. Another disadvantage of the acoustic method is that it may be used only at the cell level. Practically all applications of solar cells involve panels having many cells. It will be appreciated, therefore, that there is a need for a method for detection of micro-cracks and other defects that is quick, non-invasive and may be used at the panel level as well as the cell level. The present invention meets and exceeds these requirements.

SUMMARY OF THE INVENTION

The present invention resides a method and apparatus for detecting defects in multi-junction solar cells. In method terms, the invention may be defined as A method for detecting defects in at least one multi-junction solar cell, the method comprising illuminating at least one multi-junction solar cell with infrared radiation from a flat-panel illuminator oriented to direct the radiation onto the solar cell at a selected incident angle; positioning an infrared camera to receive specularly reflected radiation from the at least one multi-junction solar cell; and forming an image in the camera, representative of radiation specularly reflected from the at least one multi-junction solar cell, wherein any defects in the at least one solar cell are visible in the image as contrasting features.

The illuminating step employs a range of wavelengths, including a band at which the solar cell materials are relatively transparent. For example, the illuminator radiates light over a broad band of infrared wavelengths and the camera is sensitive in wavelength range of approximately 1-5 µm or 3-5 µm.

The invention can be used over a wide range of angles of incidence. For example the incident angle of illumination on the solar cell under inspection may be in the range of approximately 10° to 30° with respect a normal direction to the multi-junction cell.

The method can be used to inspect a single multi-junction solar cell, or multiple multi-junction cells that are part of a solar panel.

In terms of apparatus, the invention comprises a flat-panel illuminator, for illuminating at least one multi-junction solar cell with infrared radiation, wherein the flat-panel illuminator is oriented to direct the radiation onto the solar cell at a selected incident angle; an infrared camera positioned to receive specularly reflected radiation from the at least one multi-junction solar cell; and means for forming an image in the camera, representative of radiation specularly reflected from the at least one multi-junction solar cell. Any defects in the at least one solar cell are visible in the image as contrasting features.

It will be appreciated that the present invention represents a significant advance in the field of solar cell inspection techniques. In particular, the invention allows for the inspection of multi-junction solar cells and solar panels in a way that provides high contrast images of any cracks or other defects. Other aspects and advantages of the invention will become apparent from the following more detailed description, taken in conjunction with the accompanying drawings.

DETAILED DESCRIPTION OF THE INVENTION

Figure 1:
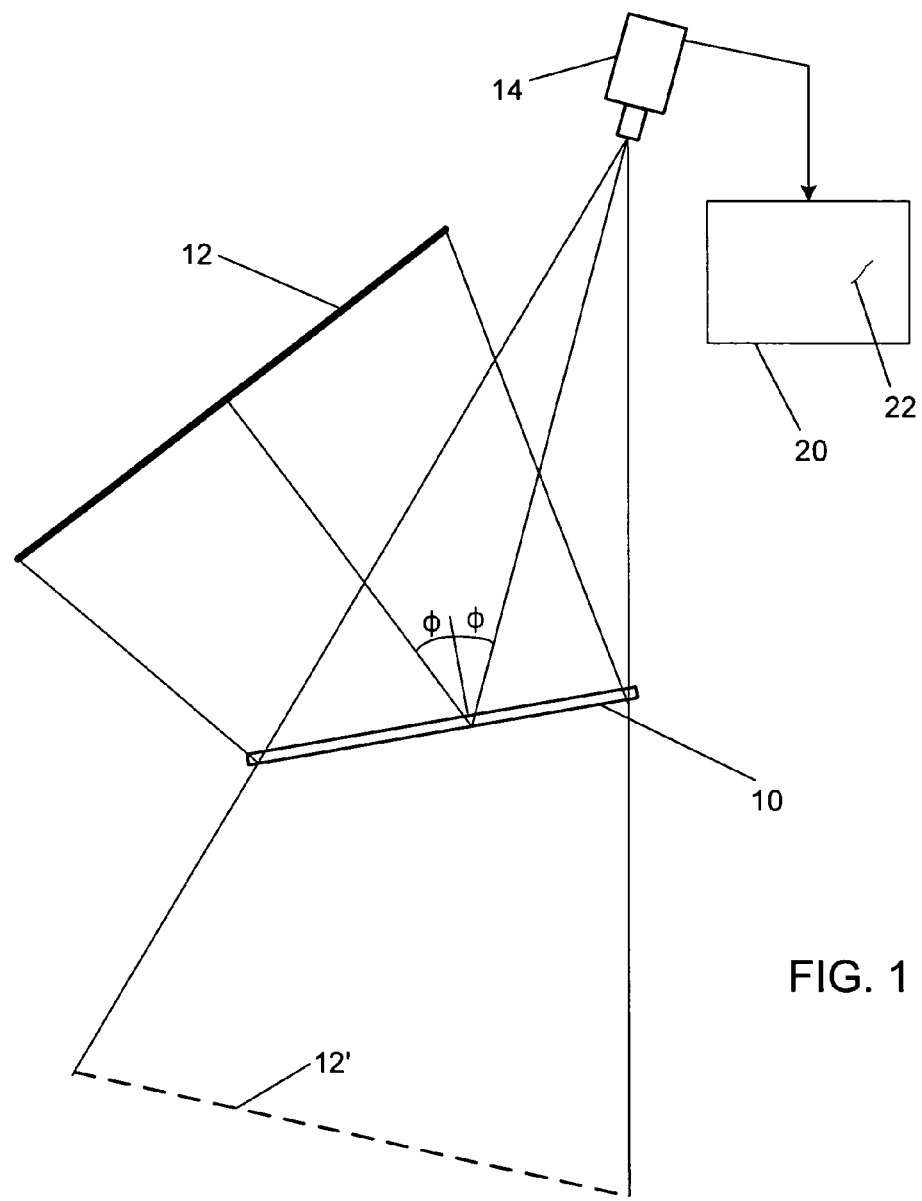
FIG. 1 is a diagram depicting the apparatus of the present invention, including an infrared illuminator and an infrared camera in relation to a solar cell or panel under inspection.

As shown in the drawings for purposes of illustration, the present invention is concerned with the detection of defects in multi-junction solar cells and panels. Although effective methods have been developed for the inspection of solar cells, such as high-efficiency silicon cells, these methods have proved ineffective for inspection of multi-junction cells, which have multiple layers of junctions in a single cell.

In accordance with the present invention, a multi-junction solar cell under inspection, indicated by reference numeral 10, is illuminated with a flat-panel infrared illuminator 12, and then inspected by means of an infrared camera 14 or other imaging device located to record specular reflections from the cell 10. Unlike some solar cells, multi-junction solar cells include a metal back plane 16, from which the infrared illumination is specularly reflected. The illuminator 12 is oriented at an angle φ to the solar cell 10, so that radiation from the illuminator has an angle of incidence φ with respect to a line drawn normal (perpendicular) to the cell. Radiation reaching the back plane 16 is secularly reflected in a direction also having an angle φ with respect to the normal direction. The camera 14 is located on and aligned with this line of reflection from the cell 10. In effect, the camera 14 sees a mirror image (indicated at 12') of the illuminator 12. The camera 14 produces an image, shown diagrammatically at 20, in which defects, and even micro-cracks, one of which is indicated at 22, are clearly visible. Because the camera image 20 is formed from specularly reflected radiation, i.e., radiation that follows essentially straight-line paths from the illuminator 12 to the cell 10 and from the cell to the camera 14, any interruption of those straight-line paths, as caused by the presence of a crack, is imaged with diminished brightness in the camera image. Thus the arrangement of the flat-panel illuminator 12 and the camera 14 aligned in the path of specular reflection from the cell 10, provides a high-contrast image of any defects or cracks encountered by radiation passing through the multiple layers of the cell. With appropriate sizing and positioning of the flat-panel illuminator 12 and the camera 14, the arrangement can be employed to inspect a broad area of a solar panel comprising multiple arrayed cells.

Figure 2:
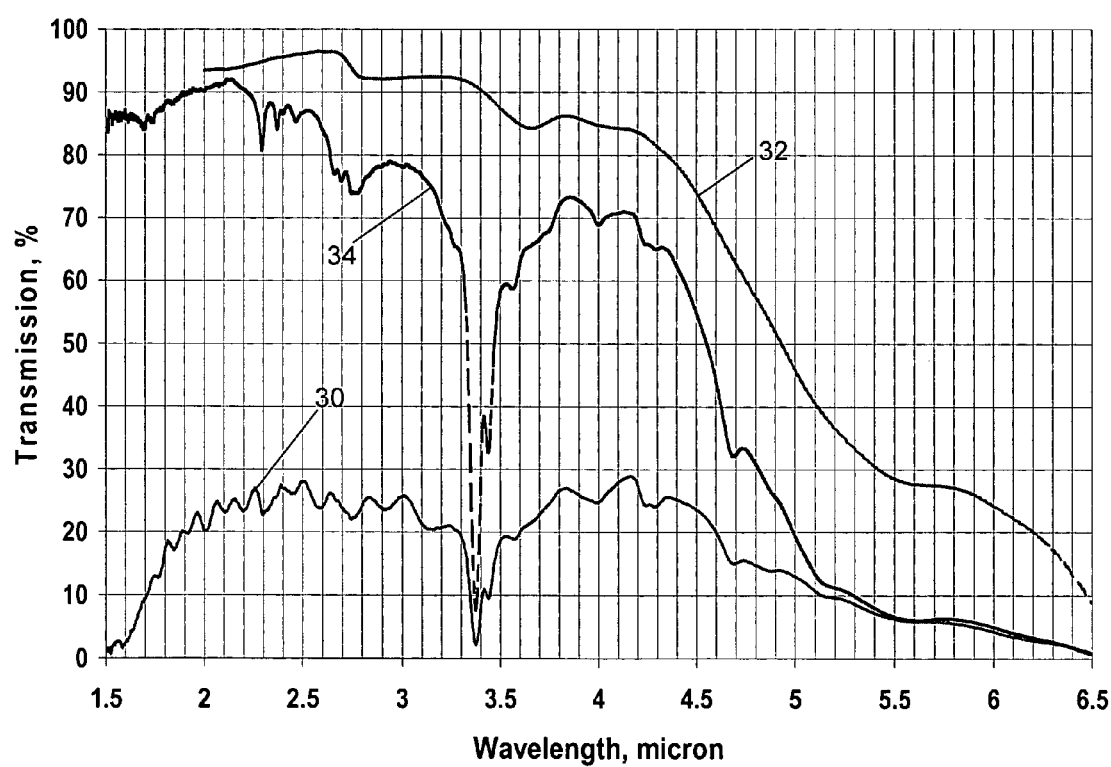
FIG. 2 is a series of graphs showing the percentage transmission through various components of a solar cell, plotted over a range of wavelengths.

FIG. 2 shows the measured percentage transmission of various components of the cell 10 over a range of infrared wavelengths. Curve 30 shows the transmission through a typical triple-junction cell, as measured with its back metal removed. It will be noted that the percentage transmission drops rapidly toward zero for wavelengths below about 2 micron (μm) and that there is a significant dip in transmission at a wavelength of about 3.4 microns. Above about 5 micron in wavelength, the percentage transmission drops gradually, to near zero at about 6.5 micron. A coverglass on the cell 10 proved to be highly transmissive over a wide range of wavelengths, at least up to 4 or 5 micron, as indicated by curve 32. Adhesives on the coverglass also had good transmission qualities at least up to 4 or 5 micron, as indicated by curve 34, but exhibited a sharp drop-off in transmission at about 3.4 micron, corresponding to the drop-off in the transmission properties of the entire solar cell shown in curve 30. The drop off below about 1.8 micron is caused mainly by the absorption of a germanium layer in the cell, whereas the drop-off beyond 4.5 micron is caused mainly by the absorption of the cover glass and the adhesive. The reflection loss at the interface of a germanium sub-layer with air as the back metal is removed may accounted for a relatively low transmission, about 28%, in the range of 1.8 to 5 micron. One therefore concludes that wavelength in the range of 1.6 to 6.5 micron, preferably in the range of 1.8 micron to 5 micron, can indeed penetrate through the substrate to reach the back metal. Additional measurements were made to confirm that radiation is reflected from the back metal mainly at a specular angle. FIG. 2 shows that there is no preferred wavelength, except for avoiding the bonding material absorption band, and that a uniform intensity infrared source would be well suited to the objects of the invention. Consistent with the transmission properties recorded in FIG. 2, the camera 14 was selected to provide infrared sensitivity in the range 3-5 microns, although an available 1-5 micron camera also provided good results.

Figure 3:
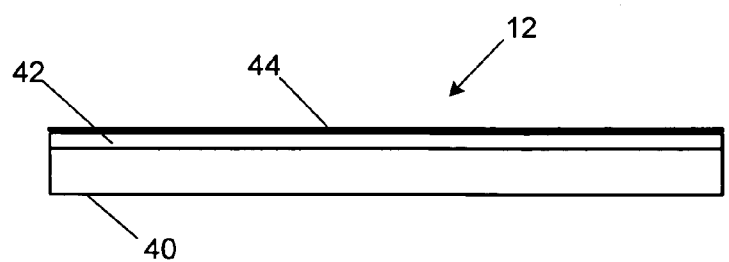
FIG. 3 is a side view of flat-panel infrared illuminator used in the apparatus of FIG. 1.

FIG. 3 shows a little more detail of the illuminator 12. It consists of a commercially available strip heater 40 on which a copper over-layer 42 approximately 0.0625 inch (1.6 mm) thick is installed to provide a more uniform distribution of heat from the strip heater. The copper over-layer 42 is painted with a high-temperature resistant black paint, as indicated at 44 to enhance the uniform radiation properties of the illuminator. The strip heater may be, for example, a mica strip heater from Watlow Electric Manufacturing Company, St. Louis, Mo. The copper plate is attached to the heater surface, by use of a high-temperature thermal conductive epoxy adhesive, to improve the uniformity of temperature of the source. An example of epoxy adhesive is Duralco 133 aluminum-filled epoxy from Contronics, located in Brooklyn, N.Y. As an alternative to painting the copper surface with a flat black paint, the surface can be coated with black chrome. The black paint or the black-chrome coating increases the emissivity and also diffuseness of the illuminator to improve its performance.

Based on the geometric ray traces one can estimate a minimum length (L) of the illuminator required for inspection, as given by:

$$L = 2(D1+D2)*X1*\cos\phi/(D1+X1*\sin\phi),$$

where $X1 = D1*\cos\phi*(\tan(\phi+\theta) - \cos\phi*\tan\phi)$

In these expressions, θ is half of the subtended angle of the camera to the solar cell 10 under inspection, and φ is the angle of the equal-angle bisector normal to the surface of the cell. X1 is the portion of the length of the cell intercepted by the equal-angle bisector. In other words, φ is the angle of incidence of a central-axis ray from the illuminator 12 onto the solar cell 10 and is also the angle of reflection, from the solar cell, of the same ray. D1 and D2 are the distance from the cell to the camera and the illuminator, respectively. A minimum width of the illuminator 12 can also be derived based on these equations using the corresponding dimensions. The actual width and length of the illuminator are preferably larger than these minimum values as determined above.

It will be appreciated from the foregoing that the present invention provides a significant improvement in the field of inspection of solar cells and panels for cracks and defects. In particular, the invention allows for the inspection of multi-junction solar cells or panels and provides a high-contrast image in which any cracks are readily discernable. It will also be appreciated that although a specific embodiment of the invention has been described by way of illustration, various modifications may be made without departing from spirit and scope of the invention. Accordingly, the invention should not be limited except as by the appended claims.

The invention claimed is:

1. A method for detecting defects in at least one multi-junction solar cell, comprising:
    illuminating at least one multi-junction solar cell with infrared radiation from a flat-panel illuminator oriented to direct the radiation onto the solar cell at a selected incident angle;
    positioning an infrared camera to receive specularly reflected radiation from the at least one multi-junction solar cell; and
    forming an image in the camera, representative of radiation specularly reflected from the at least one multi-junction solar cell, wherein any defects in the at least one solar cell are visible in the image as contrasting features, and wherein the flat-panel illuminator radiates light over a broad band of infrared wavelengths and the camera is sensitive in a wavelength of approximately 3-5 μm.

2. A method as defined in claim 1, wherein the illuminating step employs a range of wavelengths including a wavelength band at which the solar cell materials are relatively transparent.

3. A method as defined in claim 1, wherein the camera is sensitive in wavelength range of approximately 1-5 μm.

4. A method as defined in claim 1, wherein the incident angle is in the range of approximately 10° to 30° with respect to a normal direction to the multi-junction cell.

5. A method as defined in claim 1, wherein the at least one multi-junction solar cell is part of a panel of multi-junction solar cells under simultaneous inspection.

6. A method as defined in claim 1, further comprising the step of:

forming the flat-panel illuminator from a strip heater and a copper over-layer.

7. A method as defined in claim 6, wherein the step of forming the flat-panel illuminator comprises the step of:
bonding the copper over-layer to the strip heater through employment of a high-temperature thermal conductive epoxy adhesive.

8. A method as defined in claim 6, wherein the step of forming the flat-panel illuminator comprises the step of:
painting the copper over-layer with a high-temperature resistant black paint.

9. A method as defined in claim 6, wherein the step of forming the flat-panel illuminator comprises the step of:
coating a surface of the copper over-layer with black chrome.

10. Apparatus for detecting defects in at least one multi-junction solar cell, comprising:
a flat-panel illuminator, for illuminating at least one multi-junction solar cell with infrared radiation, wherein the flat-panel illuminator is oriented to direct the radiation onto the solar cell at a selected incident angle;
an infrared camera positioned to receive specularly reflected radiation from the at least one multi-junction solar cell; and
means for forming an image in the camera, representative of radiation specularly reflected from the at least one multi-junction solar cell, wherein any defects in the at least one solar cell are visible in the image as contrasting features, and wherein the flat-panel illuminator radiates light over a broad band of infrared wavelengths and the infrared camera is sensitive in wavelength range of approximately 3-5 μm.

11. Apparatus as defined in claim 10, wherein the flat-panel illuminator employs a range of wavelengths, at least some of which are relatively transparent with respect to the solar cell material.

12. Apparatus as defined in claim 10, wherein the camera is sensitive in a wavelength range of approximately 1-5 μm.

13. Apparatus method as defined in claim 10, wherein the incident angle is in the range of approximately 10° to 30° with respect a normal direction to the multi-junction cell.

14. Apparatus as defined in claim 10, wherein the at least one multi-junction solar cell is part of a panel of multi-junction solar cells under simultaneous inspection.

15. Apparatus as defined in claim 10, wherein a minimum length L of the flat-panel illuminator is defined by $$L=2(D1+D2)*X1*\cos(f)/(D1+X1*\sin(f));$$

where $X1=D1*\cos(f)*(\tan(f+\theta)-\cos f*\tan(f))$, D1 is a distance from the at least one multi-junction solar cell to the infrared camera, D2 is a distance from the at least one multi-junction solar cell to the flat-panel illuminator, $\theta$ is half of the subtended angle of the infrared camera to the at least one multi-junction solar cell, and f is the angle of the equal-angle bisector normal to the surface of the cell.

16. Apparatus as defined in claim 10, wherein the flat-panel illuminator comprises a strip heater with a copper over-layer;
wherein the copper over-layer is configured to provide a more uniform distribution of heat from the strip heater.

17. Apparatus as defined in claim 16, wherein the strip heater comprises a mica strip heater.

18. Apparatus as defined in claim 16, wherein the copper over-layer comprises a flat black paint or black chrome finish to one or more of:
enhance the uniform radiation properties of the flat-panel illuminator;
increase an emissivity of the flat-panel illuminator; and
increase a diffuseness of the flat-pane illuminator.

\* \* \* \* \*